(12) United States Patent
Francescutti et al.

(10) Patent No.: US 7,851,649 B2
(45) Date of Patent: Dec. 14, 2010

(54) PROCESS FOR THE MONONITRATION OF ALKANEDIOLS

(75) Inventors: Nevio Francescutti, San Giovanni di Casarsa (IT); Tiziano Scubla, Pasian di Prato (IT); Fausto Gorassini, Udine (IT); Graziano Castaldi, Briona (IT)

(73) Assignee: Dipharma S.p.A., Mereto di Tomba (IT)

( * ) Notice: Subject to any disclaimer, the term of this patent is extended or adjusted under 35 U.S.C. 154(b) by 305 days.

(21) Appl. No.: 12/036,555

(22) Filed: Feb. 25, 2008

(65) Prior Publication Data

US 2008/0146830 A1 Jun. 19, 2008

Related U.S. Application Data

(63) Continuation of application No. 10/534,868, filed as application No. PCT/EP03/12376 on Nov. 6, 2003, now Pat. No. 7,335,789.

(30) Foreign Application Priority Data

Nov. 14, 2002 (IT) .......................... MI2002A2410

(51) Int. Cl.
C07C 63/00 (2006.01)
(52) U.S. Cl. ..................................... 562/405
(58) Field of Classification Search ............... 562/405
See application file for complete search history.

(56) References Cited

U.S. PATENT DOCUMENTS

| 1,596,622 | A | | 8/1926 | Patrick |
| 2,294,849 | A | | 9/1942 | Olin et al. |
| 2,760,845 | A | | 8/1956 | Kanarek et al. |
| 2,981,617 | A | | 4/1961 | Hager et al. |
| 3,019,081 | A | | 1/1962 | Doss et al. |
| 3,063,945 | A | | 11/1962 | Blackwell |
| 3,113,836 | A | | 12/1963 | Blackwell |
| 5,162,568 | A | | 11/1992 | Douty |
| 5,741,432 | A | | 4/1998 | Wong |
| 5,859,053 | A | * | 1/1999 | Lesur et al. .................. 514/509 |

FOREIGN PATENT DOCUMENTS

| DE | 2039609 | 2/1972 |
| EP | 1038862 | 9/2000 |
| GB | 1040139 | 8/1966 |

* cited by examiner

*Primary Examiner*—Rei-tsang Shiao
(74) *Attorney, Agent, or Firm*—Young & Thompson

(57) ABSTRACT

A process for the preparation of compounds of formula $$HO\text{-}A\text{-}ONO_2 \qquad (I)$$

wherein A is a $C_2$-$C_6$ alkylene chain
by nitration of the corresponding alkanediols with "stabilized" nitric acid is herein disclosed.

The process is safer to operators and allows to obtain advantageous yields on an industrial scale.

4 Claims, No Drawings

PROCESS FOR THE MONONITRATION OF ALKANEDIOLS

FIELD OF THE INVENTION

The present invention provides an efficient process for the mononitration of alkanediols, which is easily controllable and safe to operators.

In particular, the invention provides a process for industrial scale production of compounds of formula

HO-A-ONO$_2$       (I)

wherein A is a straight or branched $C_2$-$C_6$ alkylene chain.

BACKGROUND OF THE INVENTION

The compounds of formula (I) are useful intermediates for the synthesis of NO-releasing non steroidal anti inflammatory drugs ("NO-NSAIDs"). Examples of NO-NSAIDs are NO-acetylsalicylic acid, NO-diclofenac, NO-naproxen, NO-ketoprofen and NO-ibuprofen. Like conventional non steroidal anti inflammatory drugs, NO-NSAIDs have antipyretic and anti-inflammatory activity, but show reduced gastrointestinal toxicity and are endowed with further useful pharmacological properties. WO 98/25918 and WO 01/10814 in particular disclose the use of compounds of formula (I) in the preparation of NO-NSAIDs.

The production of mononitrated alkanediols on an industrial scale through reduction or hydrolysis of dinitrated alkanediols is poorly selective and troublesome, as the synthesis of dinitrated alkanediols involves problems during production, storage and transport similar to those encountered with nitroglycerine.

It is well known that the mononitration of alcohols (for example glycerin) can be usually carried out with concentrated nitric acid, optionally in the presence of sulfuric acid and urea to remove nitrous acid from the reaction mixture. However, this reaction is poorly selective and quickly leads to formation of dinitrated alkanediols due to the fact that the kinetics is not easy to control. Moreover by carrying out the same reaction on short chain alkanediols strong decomposition reactions are easily triggered. WO 98/25918 also discloses alkanediols mononitration with silver nitrate or fuming nitric acid as nitrating agents, in particular with concentrated nitric acid and acetic anhydride. The mononitration of alkanediols of formula (I) with the above methods is very poorly selective and troublesome on an industrial scale. In particular, dangerous decompositions easily occur, since a strong oxidizing agent (nitric acid) is contacted with extremely unstable substrates, in particular with alkanediols wherein A is a $C_2$-$C_4$ alkylene chain.

There is therefore the need to develop a more selective and safer industrial process for the mononitration of diol compounds which also allows to obtain compounds of formula (I) in good yields.

DETAILED DESCRIPTION OF THE INVENTION

It has now been found that it is possible to selectively carry out the mononitration of alkanediols in high yield and under easily controllable conditions using "stabilised" nitric acid.

Object of the present invention is therefore a process for the preparation of a compound of formula:

HO-A-ONO$_2$       (I)

wherein A is a $C_2$-$C_6$ alkylene chain, comprising the nitration of a compound of formula

HO-A-OH       (II)

wherein A is as defined above,
with "stabilised" nitric acid.

Preferred compounds of formula (I) obtainable with the process of the invention are ethanediol-mononitrate; 1,3-propanediol-mononitrate; 1,4-butanediol-mononitrate; 1,5-pentanediol-mononitrate or 1,6-hexanediol-mononitrate, more preferably 1,4-butanediol-mononitrate.

As used herein, the term "stabilised nitric acid" means a specific preparation of nitric acid, which is a further object of the invention. This preparation consists of nitric acid diluted in water to a concentration of about 83-85%, preferably about 84.5-84.8% w/w, and is substantially free from nitrous acid and nitrogen oxides. The expression "substantially free from nitrous acid and nitrogen oxides" means that the concentration of nitrous acid and nitrogen oxides is typically lower than 10 p.p.m., preferably lower than 5 p.p.m.

Stabilization of nitric acid can be achieved by a process which comprises dilution of fuming nitric acid with water and treatment of the diluted nitric acid with an agent able to remove nitrous acid and nitrogen oxides (hereinafter referred to as "(the) agent/s"). It will be appreciated that the same result can also be obtained by adding an aqueous solution of the agent to fuming nitric acid.

Examples of agents are urea and sulfamic acid, preferably urea.

The contact time of the agents with nitric acid and their amount should be sufficient to make the nitric acid substantially free from the nitrous acid and nitrogen oxides, but should not salify an excessive amount of nitric acid, as this would lower the titre and the nitrating power. The absence of nitrogen oxides and nitrous acid in the "stabilised" nitric acid can be evaluated, for example, by visual inspection (colour), as well as by permanganate titration.

"Stabilised" nitric acid is prepared by adding 83-85% w/w nitric acid (which usually contains from about 0.06 to about 0.12% of nitrous acid and nitrogen oxides) with an amount of agent ranging from about 0.3 to about 1% w/w. To completely remove nitrous acid and nitrogen oxides the time contact with nitric acid ranges from about 80 minutes to about 130 minutes.

In the case of urea, the amount typically ranges from about 0.6 to about 1% w/w, preferably from about 0.7 to about 1% w/w and the time contact is preferably from about 95 to about 120 minutes.

The "stabilised" nitric acid according to the invention must be used within about three hours from stabilization, as relevant amounts of nitrous acid and nitrogen oxides are released again over time.

The mononitration of compounds of formula (II) with "stabilised" nitric acid is preferably carried out in a water-immiscible chlorinated organic solvent, hereinafter referred to as "chlorinated solvent". Examples of chlorinated solvents are mono-, di-, tri- and tetra-chloro $C_1$-$C_4$ alkyl hydrocarbons, preferably dichloromethane, trichloromethane, tetrachloromethane, trichloroethane and tetrachloroethane, in particular dichloromethane.

The reaction is preferably carried out by contacting a solution of the compound of formula (II) in a chlorinated solvent, with "stabilised" nitric acid dispersed in the same solvent. The solution of the compound of formula (II) should be as homogeneous as possible. For example, a homogeneous solution of 1,4-butanediol in dichloromethane can be obtained at concentrations ranging from about 60 to about 75%, preferably from about 65 to about 70% w/w.

The weight ratio of "stabilised" nitric acid to compounds of formula (II) ranges from about 10:1 to about 15:1, depending on the characteristics of the compound of formula (II).

For example, if the compound of formula (II) is 1,4-butanediol, the weight ratio of "stabilised" nitric acid to 1,4-butanediol preferably ranges from about 11:1 to about 14.5:1. Thus, the concentration of 1,4-butanediol in the nitration mixture ranges from about 2.1 to about 2.8% w/w, preferably from about 2.3 to about 2.6% w/w.

The mononitration of compounds of formula (II) is carried out at a reaction temperature lower than room temperature, preferably equal to or lower than 0° C., more preferably at 0° C., for reaction times ranging from about 10 to about 30 minutes, preferably from about 15 to about 20 minutes. The progress of the reaction can be monitored with conventional analytical methods and the optimal reaction time can thus be determined. The reaction is typically quenched with cold water (precooled to a temperature lower than about 6° C., preferably lower than about 3° C.).

The process of the invention allows to obtain the compounds of formula (I) in advantageous yields from the industrial standpoint and is definitely less hazardous than nitration with concentrated nitric acid, and optionally sulfuric acid, in the presence of urea.

As far as yields are concerned, the mononitration of 1,4-butanediol according to the invention affords 1,4-butanediol mononitrate with molar yield ranging from about 30% to about 40%, with a selectivity, expressed as percentage ratio 1,4-butanediol mononitrate/(1,4-butanediol mononitrate+1,4-butanediol dinitrate) equal to about 70-75%.

The nitration mixture, which is a further object of the invention, is a crude mixture dispersed in the organic chlorinated solvent comprising the compound of formula (I), in amount of about 2% w/w, the corresponding dinitrate by-product, the unreacted compound of formula (II) and unreacted nitric acid, and other by-products deriving from dehydration and/or oxidation. The nitration mixture is first partially neutralized with a concentrated sodium hydroxide solution. Most of the unreacted compound of formula (II) is extracted in the resulting aqueous sodium nitrate solution. The organic phase is then concentrated by evaporation of the solvent and neutralized with a diluted sodium carbonate or sodium hydroxide solution. The mixture in said chlorinated organic solvent generally contains a compound of formula (I) in amount approx. ranging from 11% to 15% w/w, the corresponding dinitrated by-product in amount approx. ranging from 3 to 4, 5% w/w; and the corresponding diol of formula (II) in amount approx. ranging from 0.2 to 0.8% w/w [compared with the compound of formula (I)]. Mixtures with total nitroesters concentrations higher than 15% w/w have explosive characteristics and are potentially hazardous to operators. The compounds of formula (I) can be separated from the corresponding dinitrated by-products and from traces of the corresponding diols of formula (II) according to known methods.

The following examples further illustrate the invention.

EXAMPLES

Example 1

Preparation of "Stabilised" Nitric Acid

A stainless steel reactor, equipped with condenser and stirrer, is loaded with 90 kg of diluted nitric acid (84.7%) having a nitrous acid content of about 0.09% and 675 g of urea beads is added under stirring. After about 90 minutes, removal of nitrous acid and nitrogen oxides is controlled by colour inspection and permanganate titration. If necessary, further urea is added in small portions.

Example 2

1,4-Butanediol-mononitrate

A stainless steel reactor is loaded in succession with 931 g of dichloromethane and 385 g of "stabilised" nitric acid. The dispersion is cooled to about 0° C. under stirring, thereafter 50 g of 1,4-butanediol in dichloromethane (70/30) is added in a single portion. The reaction mixture is kept under stirring at a temperature ranging from about −2° C. to 2° C. The kinetics of the nitration is monitored by taking samples of the mixture during the reaction. After 20 minutes the reaction is quickly quenched by pouring it into a water/ice mixture (385 g), then neutralized with 433 g of 40% NaOH, keeping the temperature below 15° C. The organic phase (980 g), which contains 1,4-butanediol-mononitrate (19.2 g), 1,4-butanediol-dinitrate (6.4 g) and 1,4-butanediol (0.1 g), is separated and concentrated to 15%. The molar yield of 1,4-butanediol-mononitrate in the crude solution amounts to 36.6%. The solution is then subjected to the subsequent purification.

The following compounds can also be obtained through the same procedure: ethanediol-mononitrate, 1,3-propanediol-mononitrate, 1,5-pentanediol-mononitrate and 1,6-hexanediol-mononitrate.

Example 3

1,4-Butanediol-mononitrate

Following the procedure described in example 2, the reactor is loaded with 21.78 kg of dichloromethane and 9 kg of "stabilised" nitric acid. The mixture is cooled to −5-0° C., then 1.26 kg of a mixture of 1,4-butanediol (0.819 kg) in dichloromethane (0.441 kg) is added under vigorous stirring in a single portion. After 18 minutes, the reaction is rapidly quenched in water (9 kg), precooled at 2° C. The solution is then neutralized with 40% sodium hydroxide (9 kg). The organic phase (23 kg), which contains 1,4-butanediol-mononitrate (0.46 kg), 1,4-butanediol-dinitrate (0.155 kg) and 1,4-butanediol (0.002 kg), is separated and concentrated to 15%. The molar yield of 1,4-butanediol-mononitrate in the crude solution amounts to 37.4%. The solution is then subjected to the subsequent purification.

The invention claimed is:

1. A process for the synthesis of a NO-releasing non steroidal anti-inflammatory drug selected from the group consisting of NO-acetylsalicylic acid, NO-diclofenac, NO-naproxen, NO-ketoprofen and NO-ibuprofen, comprising nitrating a compound of formula (II)

  (II)

wherein A is $C_2$-$C_6$ alkylene chain,
with nitric acid having a concentration ranging from 83 to 85%, and a concentration of nitrous acid and nitrogen oxides lower than 10 p.p.m., in a weight ratio of from 10:1 to 15:1 by weight respect to compound (II) for a time ranging from 10 to 30 minutes, to make a compound of formula (I)

  (I)

wherein A is as defined above,
employing said compound of formula I as an intermediate in the synthesis of a NO-releasing non steroidal anti-inflammatory drug and isolating the NO-releasing non-steroidal anti-inflammatory drug.

2. The process according to claim 1, wherein the compound of formula (I) is 1,4-butandiol-mononitrate.

3. The process according to claim 1, comprising nitration of 1,4-butanediol to produce 1,4-butanediol mononitrate.

4. The process according to claim 1, wherein the NO-releasing non-steroidal anti-inflammatory drug is NO-naproxen.

* * * * *